(12) United States Patent
Rasmussen

(10) Patent No.: US 8,085,942 B2
(45) Date of Patent: Dec. 27, 2011

(54) AUDIO APPARATUS AND METHOD FOR USE IN PROXIMITY TO A MAGNETIC RESONANCE IMAGING SYSTEM

(75) Inventor: Svein Reidar Rasmussen, Bergen (NO)

(73) Assignee: NordicNeurolab AS, Bergen (NO)

( * ) Notice: Subject to any disclaimer, the term of this patent is extended or adjusted under 35 U.S.C. 154(b) by 1117 days.

(21) Appl. No.: 11/562,752

(22) Filed: Nov. 22, 2006

(65) Prior Publication Data
US 2008/0118077 A1    May 22, 2008

(51) Int. Cl.
*H03B 29/00* (2006.01)

(52) U.S. Cl. ............ 381/71.1; 381/71.6; 381/71.7; 381/72

(58) Field of Classification Search .......... 381/71, 381/94, 67, 151, 72, 313, 326, 92, 73.1, 77, 381/93, 94.1, 94.7, 95, 71.1, 71.6, 71.7, 71.8, 381/71.11; 379/430, 406.01, 406.02, 406.03, 379/406.04, 406.05, 406.07, 406.08
See application file for complete search history.

(56) References Cited

U.S. PATENT DOCUMENTS

| | | | | |
|---|---|---|---|---|
| 4,696,030 A * | 9/1987 | Egozi | ................. | 379/167.01 |
| 5,251,263 A * | 10/1993 | Andrea et al. | ............ | 381/71.6 |
| 5,339,813 A | 8/1994 | DeYoe et al. | | |
| 5,412,419 A | 5/1995 | Ziarati | | |
| 5,427,102 A * | 6/1995 | Shimode et al. | ........ | 600/410 |
| 5,432,544 A | 7/1995 | Ziarati | | |
| 5,552,708 A | 9/1996 | Ham | | |
| 5,577,504 A | 11/1996 | Salloway et al. | | |
| 5,602,478 A | 2/1997 | Salloway et al. | | |
| 5,627,902 A * | 5/1997 | Ziarati | ................. | 381/385 |
| 5,631,965 A | 5/1997 | Chang et al. | | |
| 5,861,865 A | 1/1999 | Anand et al. | | |
| 5,864,331 A | 1/1999 | Anand et al. | | |
| 5,877,732 A | 3/1999 | Ziarati | | |
| 6,567,524 B1 | 5/2003 | Svean et al. | | |
| 7,039,195 B1 | 5/2006 | Svean et al. | | |
| 7,571,006 B2 * | 8/2009 | Gordon et al. | ............. | 607/57 |
| 2004/0086138 A1 * | 5/2004 | Kuth | ................ | 381/72 |
| 2005/0197565 A1 | 9/2005 | Yagi et al. | | |
| 2007/0280491 A1 * | 12/2007 | Abolfathi | ................. | 381/313 |

FOREIGN PATENT DOCUMENTS

| | | |
|---|---|---|
| EP | 0 644 436 A1 | 3/1995 |
| EP | 0 655 730 A1 | 5/1995 |
| GB | 2 265 790 A | 10/1993 |

OTHER PUBLICATIONS

International Search Report issued in counterpart International Application No. PCT/IB2007/003521, mailed Apr. 11, 2008.
Written Opinion issued in counterpart International Application No. PCT/IB2007/003521, mailed Apr. 11, 2008.
First Examination Report issued in EP 07825684.9 on Mar. 10, 2011.

* cited by examiner

*Primary Examiner* — Vivian Chin
*Assistant Examiner* — Leshui Zhang
(74) *Attorney, Agent, or Firm* — DLA Piper LLP US

(57) ABSTRACT

An apparatus and method for presenting high-quality auditory stimuli, receiving patient communication and providing noise cancellation within the environment of magnetic resonance imaging ("MRI") equipment. A microphone is positioned in a noise attenuated channel for recording of the patient's voice. A microphone is disposed outside of a noise attenuated channel to directly record the sounds of MRI equipment during its operation. The signals generated by the microphones are employed to reduce the output of noise generated by MRI equipment.

10 Claims, 7 Drawing Sheets

AUDIO APPARATUS AND METHOD FOR USE IN PROXIMITY TO A MAGNETIC RESONANCE IMAGING SYSTEM

BACKGROUND OF THE INVENTION

1. Field of the Invention

The present invention relates to devices that are used in conjunction with Magnetic Resonance Imaging ("MRI") equipment to provide stimuli or entertainment for a patient and to facilitate communication with a patient during an MRI diagnostic treatment or imaging process.

2. Description of the Related Art

MRI has become a preferred technology for generation of high quality images of different tissue types within the human body. Headphone devices to provide auditory stimulation or entertainment for the patient have been developed and improved for use within MRI equipment. The signals that are to be reproduced by the headphones may originate as music or similar entertainment content, communications from the MRI operator to the patient, or patient auditory stimuli used in functional MRI ("fMRI") and other brain function imaging.

The headphone devices must be able to operate within the MRI environment. The MRI environment typically produces intense magnetic fields and further relies on measurement of small radio-frequency signals created by the response of human tissue to stimulation by radio-frequency signals and other magnetic fields. The MRI environment is also confined by the dimensions of the MRI equipment. More specifically, most MRI equipment includes a bore into which the patient is moved during the imaging operation.

Devices operable to sense sound made by the patient are also implemented in the MRI environment. These devices are generally adapted to allow the patient to communicate with the operator of the MRI equipment and provide a way for the operator to confirm that the patient is relaxed and comfortable. Devices used to receive the sound from the patient must also be compatible with the MRI environment.

The MRI equipment is prone to generating significant amounts of noise during operation. This noise may be created in part by the rapid changes in the current that cause vibration such that knocking can be heard by the patient. The noise generated by MRI equipment is typically loud and is generated across a broad frequency spectrum. Additionally, the noise generated varies in intensity during operation of the MRI equipment. The presence of this noise presents the possibility of injury to the patient's hearing, which has been avoided through use of headphones and/or earplugs.

SUMMARY OF THE INVENTION

According to one aspect of the invention, a sound system is described that can be used within the magnetic field associated with MRI equipment that includes a structure formed of a rigid housing and pliable material that can form a channel when placed in contact with the human ear and an audio control circuit. The rigid housing includes a speaker and a microphone that is positioned within the structure such that each are within the channel formed. The audio control circuit partially removes sound generated from the speaker from the signal received from the microphone.

According to another aspect of the invention, a noise cancellation system is set forth for use within the fields associated with MRI equipment that comprises a control unit for processing acoustic signals between a patient and an operator. The system includes an attenuator to provide a degree of acoustic insulation that is formed to create a channel with the ear of the patent. A first microphone is included that is located outside of the channel formed by the attenuator and the patient's ear and provides input to the control unit. A second microphone is connected as input to the control unit and a speaker is connected as output from the control unit which are each located within the channel.

According to another aspect of the invention, a method is provided that performs error correction of auditory signals presented to a patient located within the fields associated with MRI equipment that combines an input signal associated with the noise made by MRI equipment with an output signal such that the output signal substantially cancels the sound made by the MRI equipment. Further, the method creates a second input signal by sensing the sound made by the speaker and compares the second input signal to the first input signal to adjust the combination to further cancel the sound made by the MRI equipment.

DETAILED DESCRIPTION OF SEVERAL EMBODIMENTS

Figure 1:
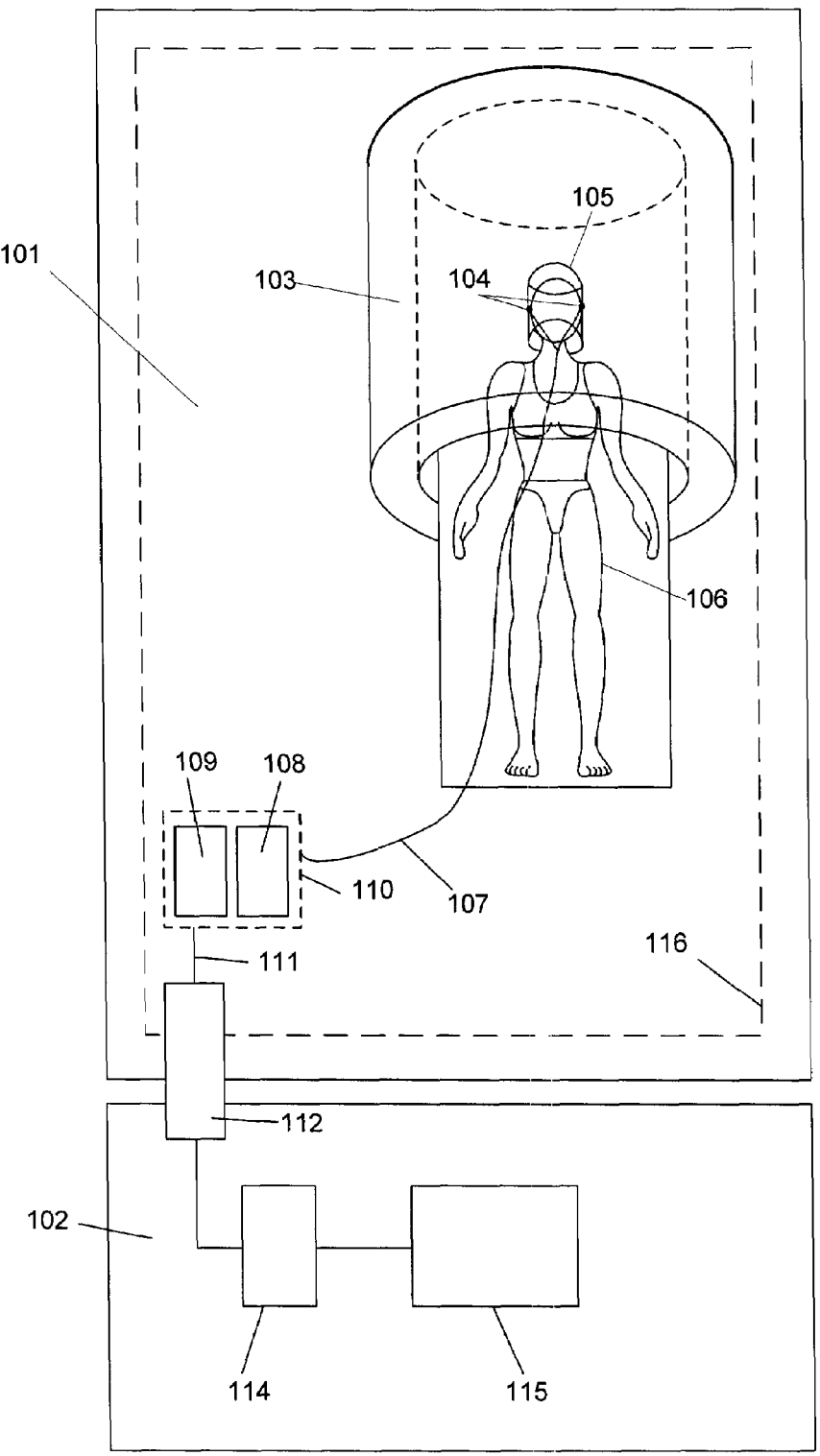
FIG. 1 shows the positioning of the earphones and electronics with respect to MRI equipment.

The following detailed description outlines an MRI-compatible audio system for reproducing and recording sound within the magnetic and RF fields generated by MRI equipment using an earphone device. As shown in FIG. 1, the MRI equipment is typically installed in at least two rooms. The magnet room 101 houses the magnet portion of the MRI equipment 103 along with the RF head coil 105 when necessary and the patient 106. The magnet room 101 is typically surrounded by a Faraday cage 116 that effectively insulates the interior of the magnet room from electromagnetic fields and signals from the outside environment. The control room 102 houses at least a portion of the control electronics (not shown) and provides means for the operator to observe the patient while supervising the procedure. The control electronics within the control room include user interfaces (not shown) to facilitate control of the procedure.

FIG. 1 includes the earphones 104 that are worn by the patient 106 during the operation of the MRI equipment. The earphones 104 may be positioned inside the bore and include an electrical connection through shielded cable 107 to a housing 110 that is comprised of a Faraday cage to effectively isolate the contents of the housing from the magnet room 101. Within the housing 110, there is an audio system control unit 108 that receives an electrical signal from the fiber optic transceiver unit 109, which converts a light signal from the control room 102 into an electrical signal. The fiber optic transceiver unit 109 is connected to another fiber optic transceiver unit 114 through a fiber optic cable 111 that is passed through a wave guide 112. The dimensions of the wave guide 112 are calculated so that only non-disturbing frequencies will enter the magnet room 101. The wave guide 112 is typically a tube mounted on the Faraday cage 116 that surrounds the magnet room 101. Within the control room 102, the fiber optic transceiver 114 is electrically connected to the audio input/output source 115 for the system.

Figure 2:
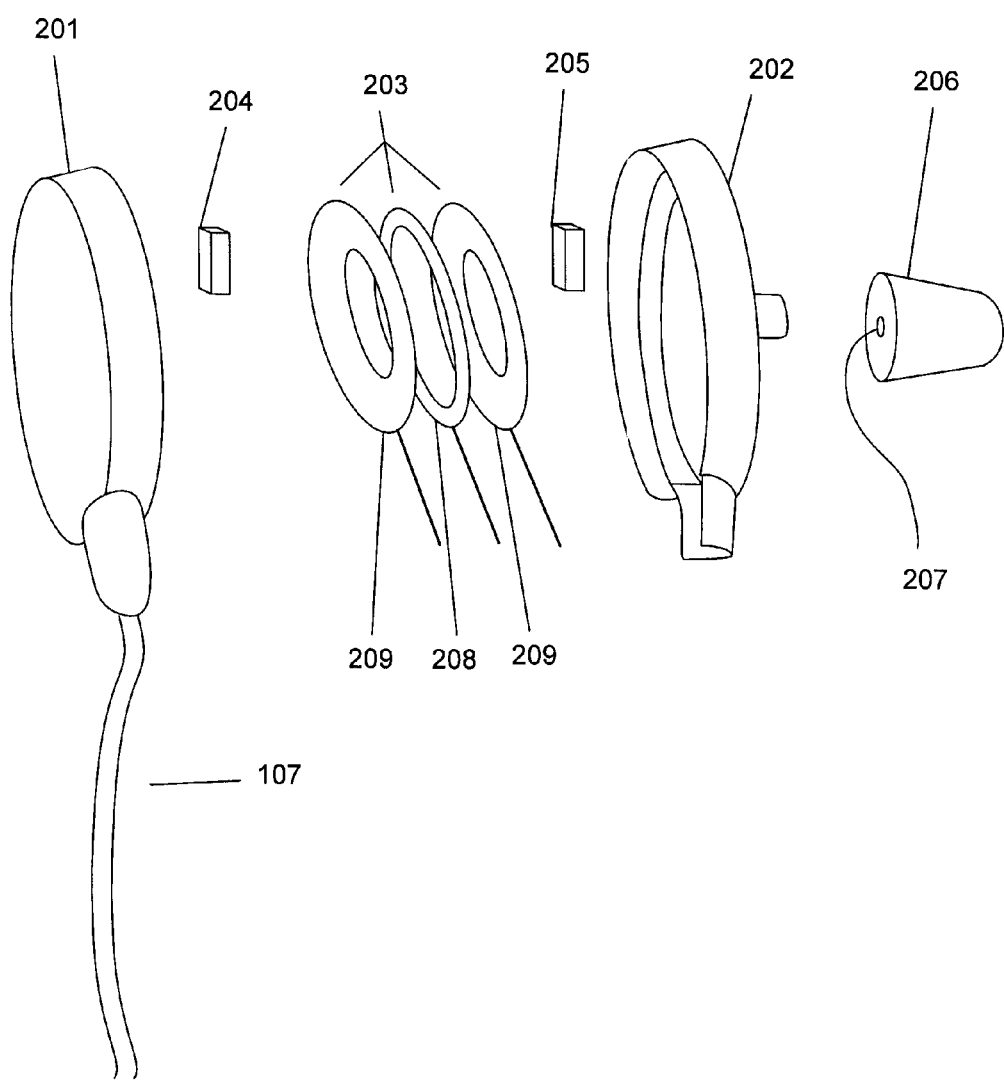
FIG. 2 is a cross-sectional view of an embodiment of an earphone assembly.

Referring to FIG. 2, an earplug 104 is formed by a housing 201-202. The earplug housing optimally is shaped for placement adjacent to the head of the patient to have minimal obstruction of the RF head coil, if one is used. Within the earplug housing, there is a speaker element 203 that reproduces sound for the patient. The speaker element 203 may be formed from a membrane 208 and two stators 209. The stators 209 are reference points for the moveable membrane 208. The audio signal is transformed into two high-voltage signals within the audio system control unit 108. These signals will typically have identical power and phase and are connected to each stator 209 which results in the generation of an electrostatic field. This field will work either with or against the membrane 208 to generate sound. Other speaker elements that reduce the use of magnetic materials and that are sufficiently shielded may be substituted for the electrostatic speaker element 203.

The housing 201, 202 also contains at least one microphone 205. The microphone 205 may be placed inboard of the speaker 203 toward the patient 106 in the housing part 201, 202, thus ensuring best performance in picking up patient communication. Microphone 205 records the patient's voice and otherwise provides a signal for use in error correction of the active noise cancellation process discussed with reference to FIGS. 5 and 6. The microphone 205 is positioned within the housing 201, 202 such that it is within a channel 207 that is defined when the earplug 104 is put in contact with the patient's ear. This channel 207 is formed whether the housing 201, 202 is formed to be inserted into the ear canal or is outside of the ear canal but is otherwise in contact with the ear of the patient. This channel 207 is any space that is defined by the contours of the patient's ear, the material implemented for noise attenuation 206 and the components of the earplug such as the speaker element 203 and microphone 205.

A second microphone 204 may also be implemented to record background noise. The second microphone 204 may be placed in the housing 201, 202 facing outwards. This is done so it can pick up the environmental noise related to the surrounding sound from the MRI equipment with best performance, and with minimal disturbance from the speaker element 203. This microphone 204 may simply be positioned within the housing 201, 202 without any aperture to the environment, or may be implemented with a dedicated aperture 303 (see FIGS. 3A and 3B) to more directly receive noise generated by the MRI equipment.

The microphones 204, 205 that can be in this environment include micro-machined silicon ("MEMS") microphones. MEMS microphones are made of poly-silicon and manufactured using semiconductor manufacturing processes that result in a robust microphone that yields a high degree of repeatability and stable acoustic performance. Other microphones that reduce the use of magnetic materials and that are sufficiently shielded may also be used.

On the side of the housing 202 facing the patient's ear, there is a material 206 designed to fit into the inner part of the patient's ear and result in reducing the noise perceptible to the patient from the environment. This material can be replaceable. FIG. 2 shows replaceable material 206 that is shaped to contact the patient's ear. The replaceable material 206 may be formed from foam with known acoustic properties or from other materials, including soft plastic that can seal within the patient's ear and provide noise attenuation. The material 206 may be shaped such that it defines a channel 207 when put in contact with the patient's ear within which environmental noise is effectively attenuated. Channel 207 may be a single path to the patient's ear with equal access by the speaker element 203 and the microphone 205 as shown in FIG. 2.

Figure 3A:
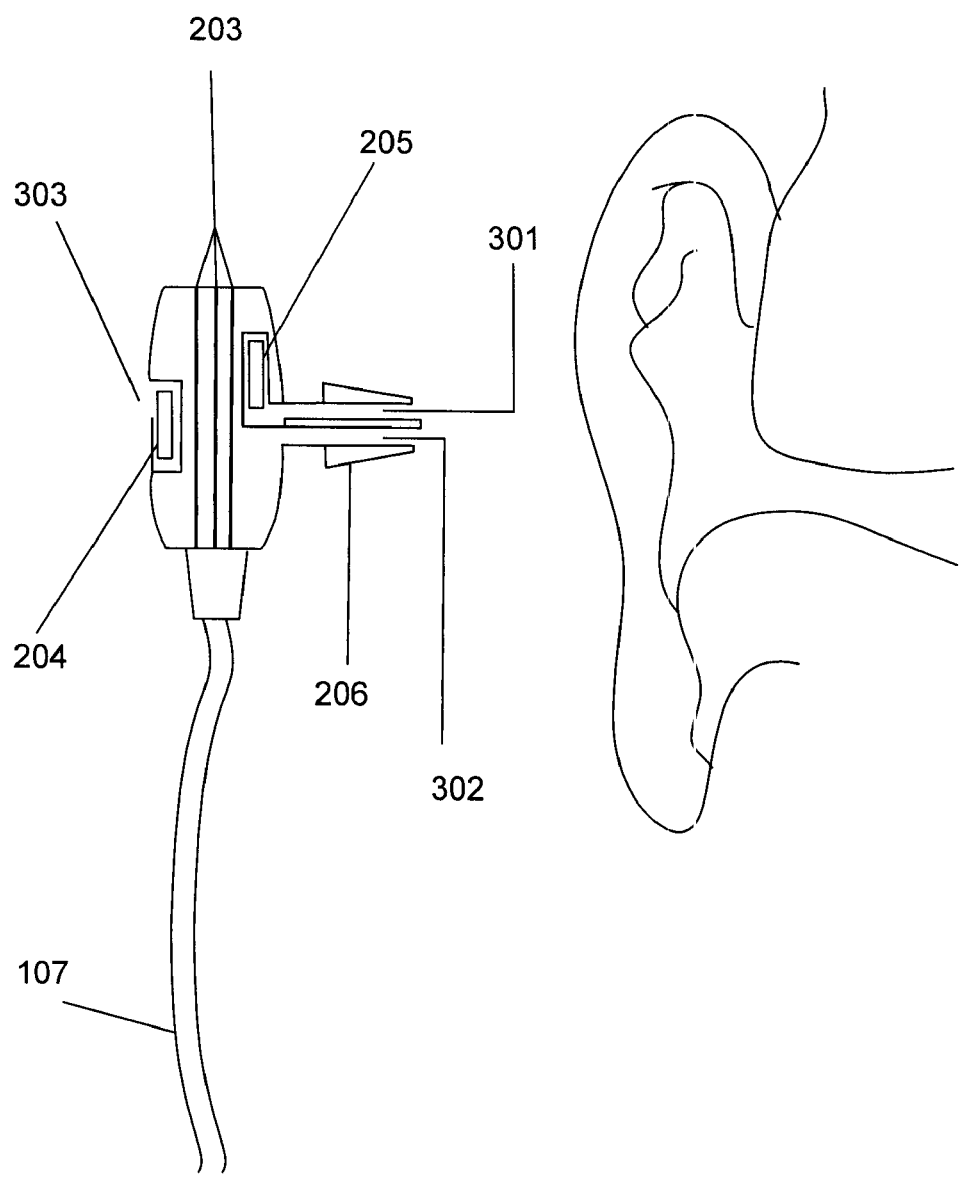
FIGS. 3A and 3B provide details of an embodiment of the channel formed for noise attenuation.
Figure 3B:
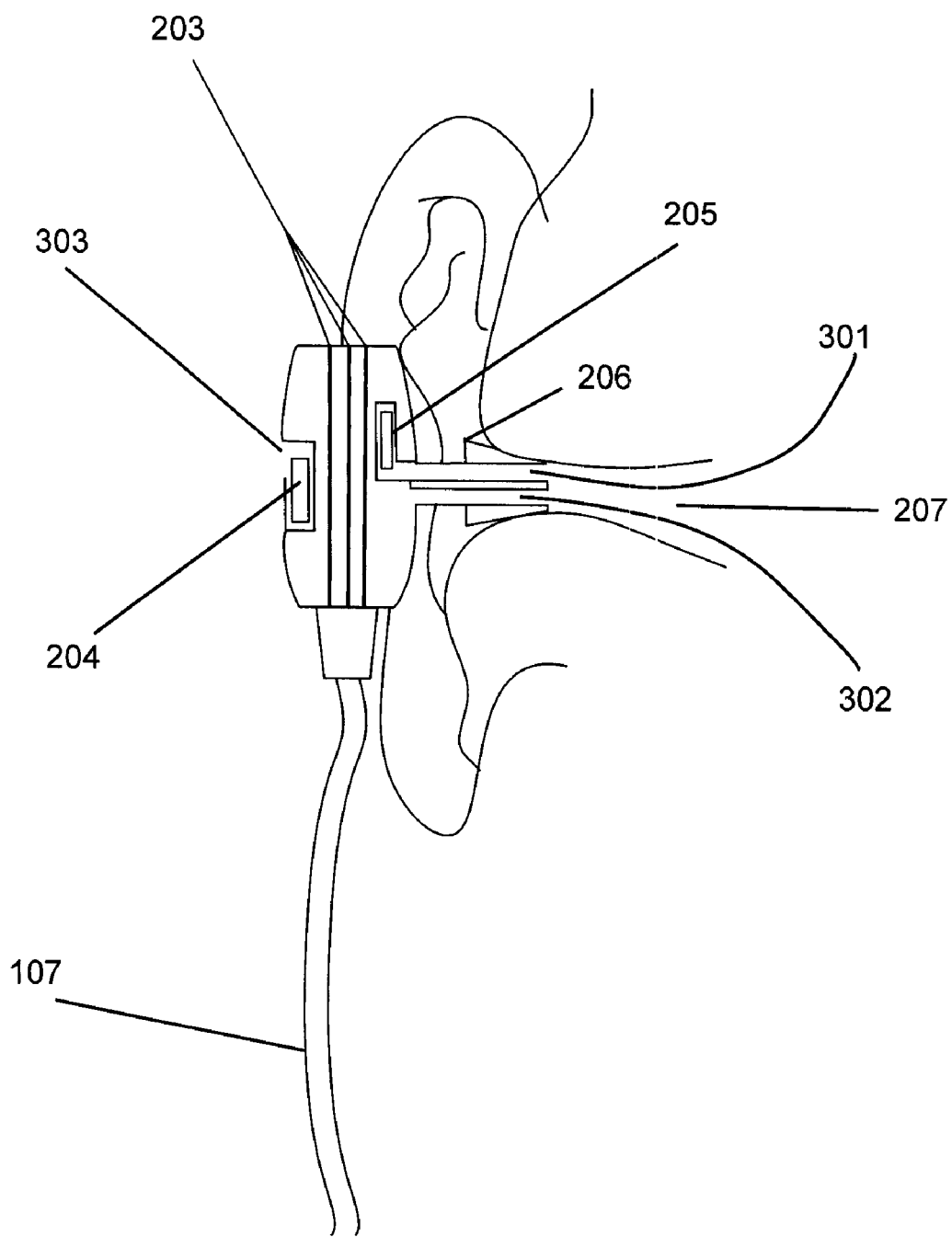

Alternatively, FIGS. 3A and 3B show an embodiment wherein the channel 207 is formed of two tubes, one tube 302 being coupled to the speaker element and the other tube being coupled to the microphone 205. These tubes may be kept separate as long as possible to achieve minimal disturbance between the auditory stimulus presented by the speaker 203 and the patient's communication picked up by the microphone 205.

Figure 4:
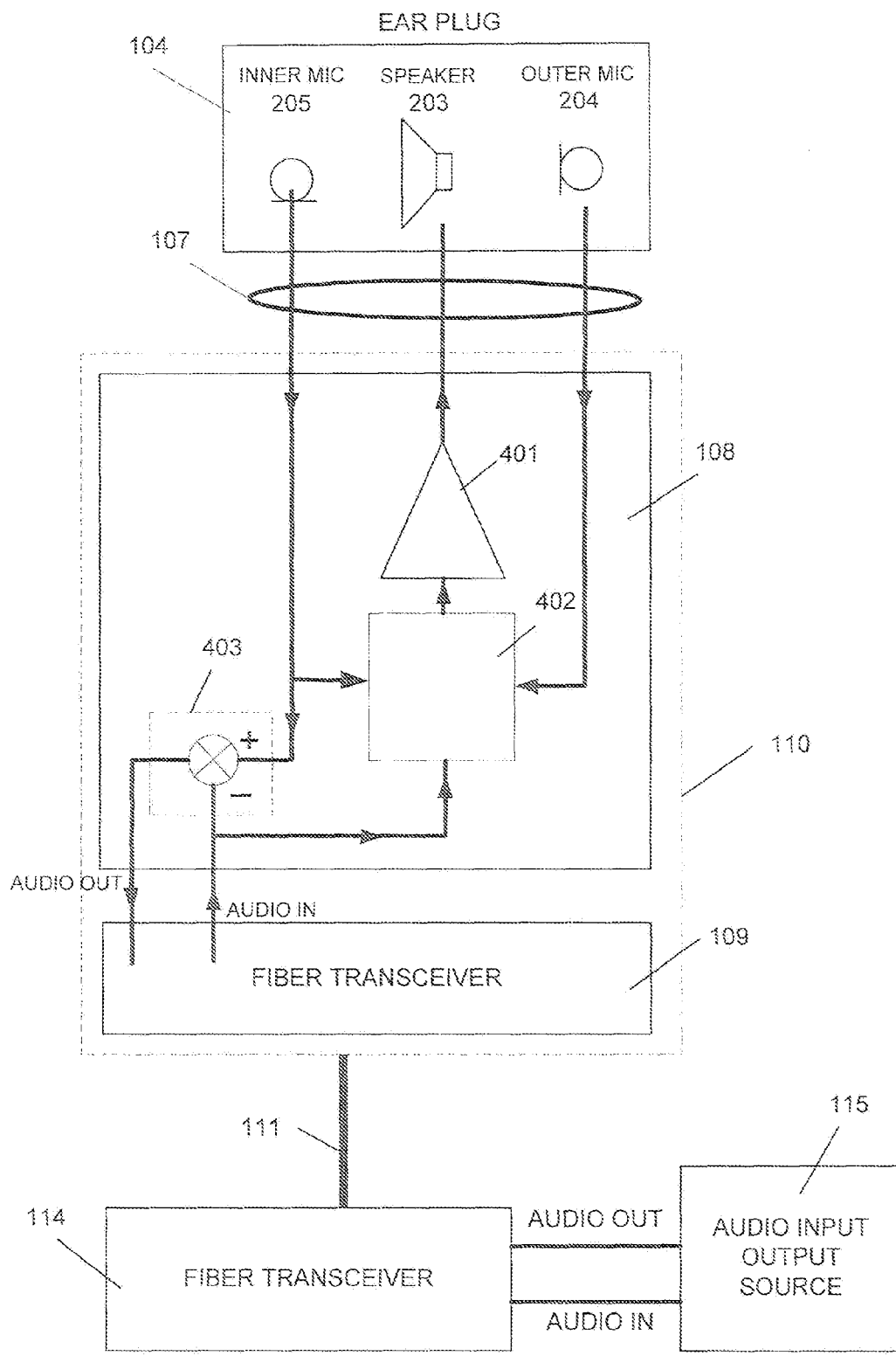
FIG. 4 is a block diagram of the electronic components including the microphones and speaker element and the supporting electronics.

Referring to FIG. 4, active noise cancellation and error correction constitutes a portion of the audio system control unit 108. Within the audio system control unit 108, there are audio cancellation electronics 402, 403 and an amplifier 401 that amplifies the electrical signal. The audio system control unit may produce if necessary the positive and negative high voltage delivered to the speaker element 203 described above. The signal enters the speaker element 203 through a shielded cable 107, which may be split into two shielded cables, one for the left and one for the right.

Active noise cancellation is accomplished by adding filtered and inverted sound from the microphone 204 to the auditory stimuli presented to the patient. The sound from the microphone 204 can be filtered to remove high frequency portions of the signal. The signal recorded by the microphone 204 represents the noise generated by the MRI equipment. Thus the surrounding sound can effectively be taken out of the auditory signal presented to the patient. To optimize the noise cancellation, the sound from the inner microphone 205 may be used as a feedback to the noise cancellation unit 402. An error correction for this active noise cancellation is performed by using the signal from the microphone 205 to correct for the mismatch between the noise picked up by the outer microphone 204 and the noise recorded inside the channel 207 formed by contact with the ear of the patient. Because of the distance between the two microphones and their positioning, the sound from the microphone 205 is time-delayed and filtered before it is compared with the microphone 204 for error correction.

The noise processing component 403 also is operative on the signal that is recorded by the microphone 205 that represents the voice of the patient 106. Before the signal from the microphone 205 is sent to the optic transceiver unit 109 it is cleared of the auditory stimuli presented to the patient coming from the auditory input output source 115. Cancellation is achieved by subtracting the auditory stimuli from the signal from microphone 205 before it is sent to the optic transceiver 109. By this, active noise cancellation of the signal representing the patient's voice is achieved and a clearer representation of the patient's communication is accomplished.

Figure 5:
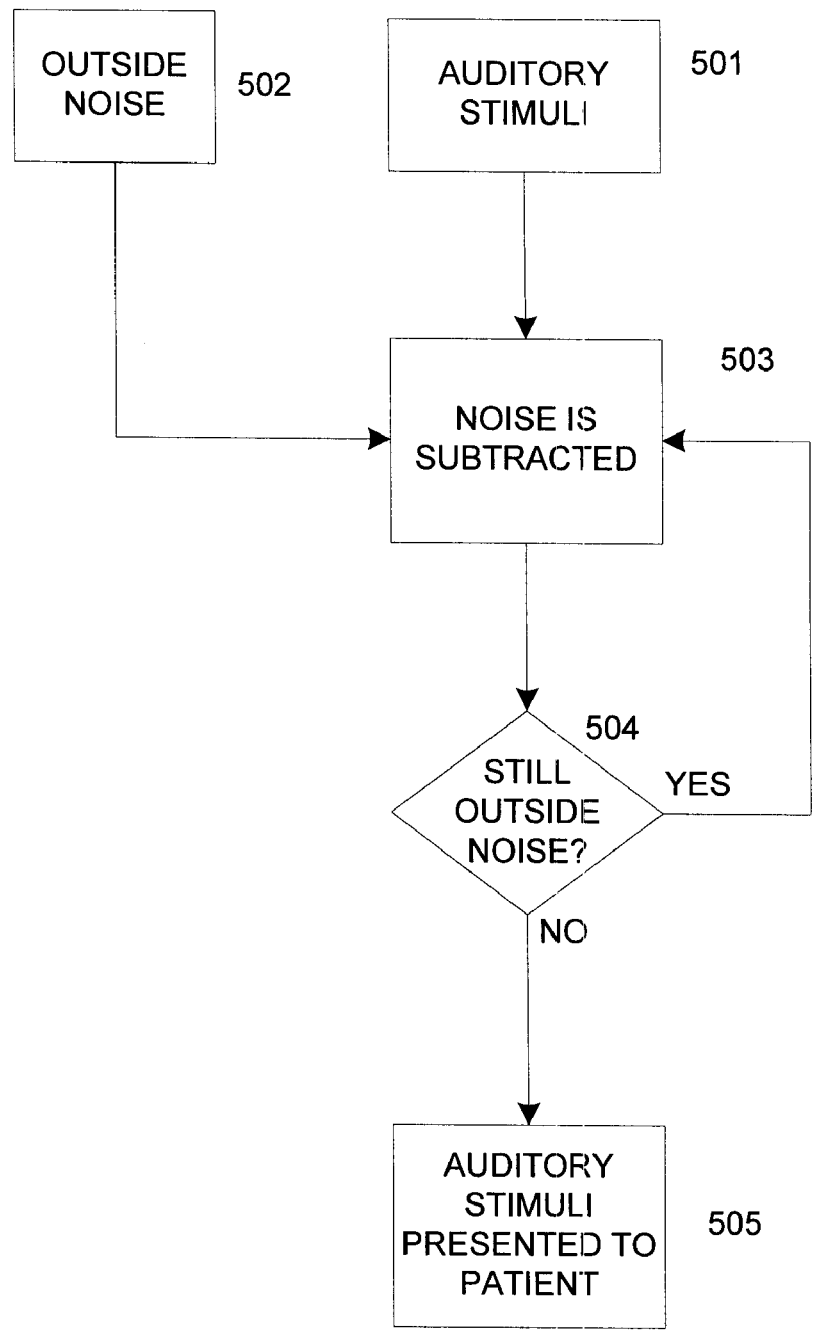
FIG. 5 is a flowchart illustrating the steps to process the auditory signal for reproduction for the patient; and, FIG. 6 is a flowchart illustrating the steps to process sounds made by the patient.

Referring to FIG. 5, the auditory stimulation that is to be provided to the patient is processed consistent with the operation of the audio control unit 108. The auditory stimuli is first input 501 through the fiber optic transceiver 109. In addition to this input, the recorded signal from the microphone 204 located outside of the noise attenuation material 206 is provided 502. The signal from the microphone 204 is then subtracted from the stimuli 501 such that the signal will include active noise cancellation. The resulting signal is then evaluated 504 to determine whether outside noise is still present. This evaluation may be accomplished by comparing the sound output to the patient within the channel 207 which is recorded by microphone 205 to the signal that is desired to be reproduced. If microphone 205 records sound that is consistent with noise from the operation of the MRI equipment, then the noise signal may be amplified to achieve an improved result. As the signal is determined to have achieved the desired amount of noise reduction, the signal resulting from the subtraction 503 is presented to the patient 505.

Figure 6:
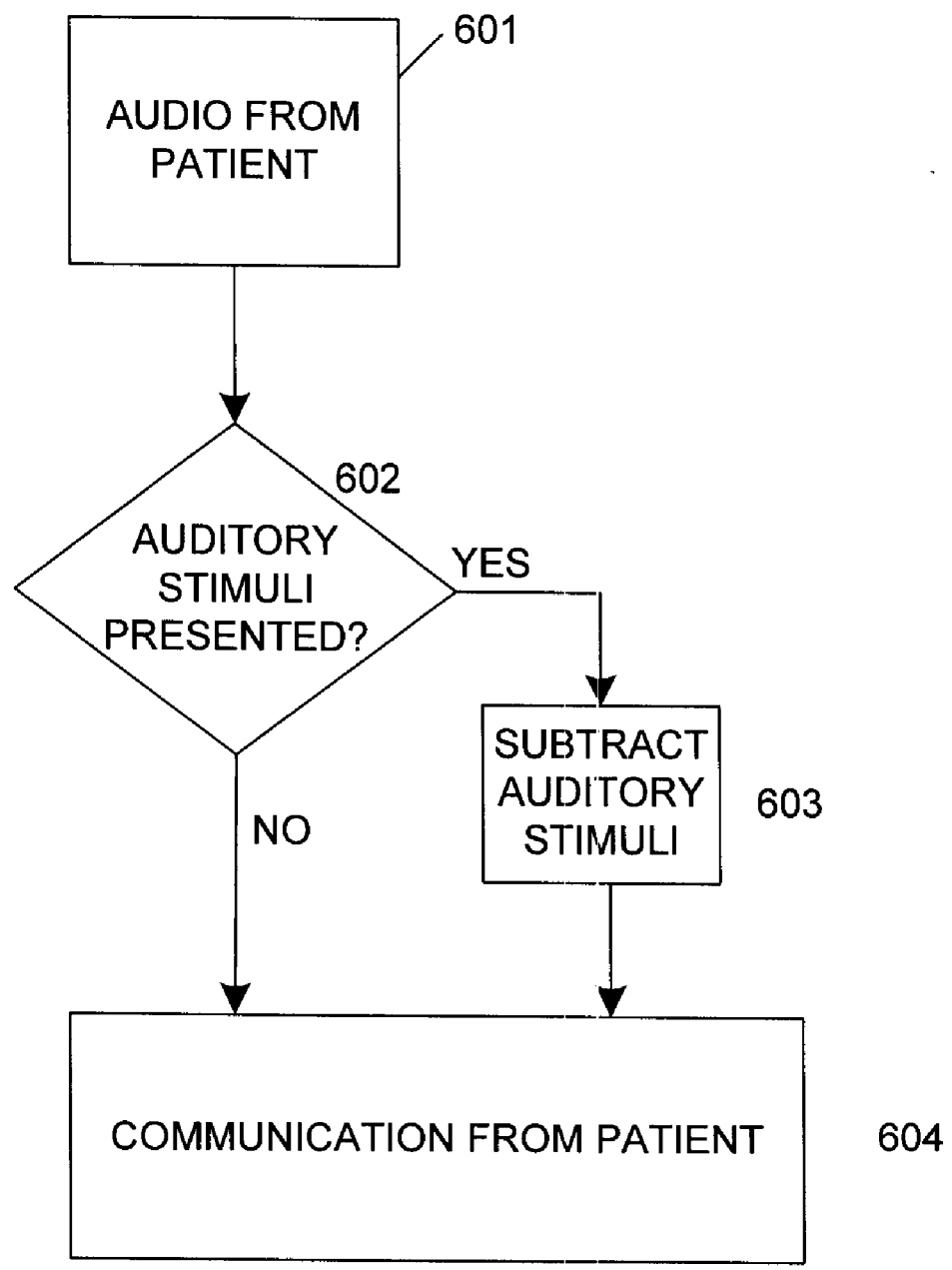

Referring to FIG. 6, the recorded sound that includes the patient's voice is processed to remove an effective amount of the auditory stimuli that is presented to the patient. The recorded signal has the benefit of being recorded in the channel 207 that provides noise attenuation and noise cancellation through the process described in FIG. 5. Additionally, this processing will evaluate whether auditory stimulation was present 602. If so, the process will subtract the auditory stimuli signal from the recorded signal 603. The resulting signal that contains the voice of the patient can be forwarded to MRI equipment operator 604 with benefits of having removed undesired portions of the signal.

What is claimed is:

1. A sound system for use within magnetic fields produced by magnetic resonance imaging equipment, comprising:
   a rigid housing and molded pliable material shaped such that said material is configured to form a channel when placed in contact with an ear;
   a microphone positioned to be within the channel and to be in fluid communication with a canal of the ear when the molded pliable material is placed in contact with the ear;
   a speaker positioned to be within the channel and to be in fluid communication with a canal of the ear when the molded pliable material is placed in contact with the ear; and
   an audio control circuit to alter a signal from the microphone by subtracting a signal used to power the speaker such that sound produced by the speaker is reduced, wherein
   the channel is a space defined by contours of the ear, the molded pliable material, the microphone and the speaker, and
   the rigid housing, the molded pliable material, the microphone and the speaker are constructed and arranged to be used in magnetic resonance imaging equipment.

2. The device of claim 1 further comprising:
   a second microphone positioned to be outside of the channel.

3. The device of claim 2 further comprising:
   a second audio control circuit electrically connected to said second microphone and said speaker operable to subtract a signal received from said second microphone from an input signal for said speaker to result in a modified input signal to said speaker that reduces the sound outside of said channel presented to the human ear.

4. The device of claim 3 further comprising:
   a third audio control circuit electrically connected to said microphone to be positioned within the channel, the input signal for said speaker, and the second microphone, said third audio control circuit being capable of comparing the signal received from said second microphone with the signal from said microphone positioned within the channel to determine whether noise created by magnetic resonance equipment present within said channel was reduced.

5. The device of claim 4, wherein said molded pliable material is formed to provide a first region associated with said speaker and a second region associated with said microphone within the channel.

6. A noise cancellation system for use within magnetic fields produced by magnetic resonance imaging equipment, comprising:
   a control unit for processing acoustic signals between a patient and an operator;
   an acoustic attenuator formed to be positioned in contact with an ear of the patient for forming a channel when placed in contact with the ear of the patient;
   a first microphone connected as input to said control unit positioned to be outside of said channel;
   a speaker connected as output to said control unit positioned to be inside of said channel and in fluid communication with a canal of the ear of the patient when the acoustic attenuator is placed in contact with the ear; and,
   a second microphone that is connected as input to said control unit and positioned to be inside of said channel and in fluid communication with a canal of the ear of the patient when the acoustic attenuator is placed in contact with the ear, for sensing sound made by the patient, wherein
   the channel is a space defined by the contours or the ear of the patient, the acoustic attenuator material, the speaker and the second microphone, and
   the acoustic attenuator, the second microphone and the speaker are constructed and arranged to be used in magnetic resonance imaging equipment.

7. The system of claim 6, wherein the control unit is capable of creating a modified input speaker signal by combining a signal from said second microphone with the electrical signal received to drive the speaker such that noise created by magnetic resonance equipment present within the channel is reduced.

8. The system of claim 6, wherein the control unit subtracts the modified input speaker signal from a signal from the second microphone for output to the operator.

9. The system of claim 6, wherein said attenuator is formed to provide a first region associated with said speaker and a second region associated with said second microphone inside of said channel.

10. A method of performing error correction of auditory signals presented to a patient located within magnetic fields created by MRI equipment, comprising:
    receiving a raw output signal intended for presentation to the patient through a speaker positioned within the fields created by the MRI equipment;
    creating a first input signal by sensing sound made by the MRI equipment by a first microphone;
    creating a second input signal by sensing the sound made by the speaker by a second microphone;
    using the second input signal and the first input signal to modify the raw output signal to cancel sound made by the MRI equipment, wherein the speaker and the second microphone are positioned in a channel which is in fluid communication with a canal of an ear of the patient when the second microphone and the speaker are used in the MRI equipment.

* * * * *